(12) United States Patent
Shetty et al.

(10) Patent No.: US 8,383,147 B2
(45) Date of Patent: Feb. 26, 2013

(54) REINFORCED ABSORBABLE SYNTHETIC MATRIX FOR HEMOSTATIC APPLICATIONS

(75) Inventors: Dhanuraj S. Shetty, Jersey City, NJ (US); Olajompo Moloye-Olabisi, Neshanic Station, NJ (US); Robert W. Van Holten, Flemington, NJ (US); Degang Zhong, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/591,501

(22) Filed: Aug. 22, 2012

(65) Prior Publication Data

US 2012/0315316 A1    Dec. 13, 2012

Related U.S. Application Data

(62) Division of application No. 12/781,103, filed on May 17, 2010, now Pat. No. 8,273,369.

(51) Int. Cl.
| | |
|---|---|
| A61F 2/00 | (2006.01) |
| A61F 13/00 | (2006.01) |
| A61L 15/16 | (2006.01) |
| A61K 38/00 | (2006.01) |
| A61K 38/36 | (2006.01) |
| A61K 47/30 | (2006.01) |

(52) U.S. Cl. ....... 424/444; 424/426; 424/447; 514/13.5; 514/13.6; 514/13.7; 514/13.8; 514/14.7; 514/772.3; 602/45; 602/50; 606/908

(58) Field of Classification Search .......... None
See application file for complete search history.

(56) References Cited

U.S. PATENT DOCUMENTS

| | | | |
|---|---|---|---|
| 3,364,200 | A | 1/1968 | Ashton et al. |
| 4,626,253 | A | 12/1986 | Broadmax, Jr. |
| 4,741,337 | A | 5/1988 | Smith et al. |
| 5,180,398 | A | 1/1993 | Boardman et al. |
| 5,393,594 | A | 2/1995 | Koyfman et al. |
| 5,593,441 | A | 1/1997 | Lichtenstein et al. |
| 5,686,090 | A | 11/1997 | Schilder et al. |
| 6,762,336 | B1 | 7/2004 | MacPhee et al. |
| 7,666,803 | B2 | 2/2010 | Shetty et al. |
| 2004/0078077 | A1 | 4/2004 | Binette et al. |
| 2006/0084338 | A1 | 4/2006 | Shetty et al. |
| 2006/0084930 | A1 | 4/2006 | Dhanaraj et al. |
| 2008/0033333 | A1 | 2/2008 | MacPhee et al. |
| 2009/0246238 | A1 | 10/2009 | Gorman et al. |
| 2010/0331864 | A1 | 12/2010 | Shetty et al. |

OTHER PUBLICATIONS

International Search Report re: PCT/US11/36590 dated Sep. 9, 2011.
Holcomb et al., Dry Fibrin Sealant dressings reduce blood loss, resuscitation volume and improve survival in hypothermic coagulopathic swine with grade V liver injuries, J. Trauma, 1999; 47:233.
Holcomb et al., Efficacy of dry fibrin sealant dressing for hemorrhage control after ballistic injury, Arch Surg., 1998; 133:32.
Holcomb et al., Implications of new dry fibrin sealant technology for trauma surgery, Surg. Clin. North Am., 1997; 77:943.
Kheirabadi, B. et al, 'The Potential Utility of Fibrin Sealant Dressing in Repairing of Vascular Injury in Swine' Journal of Trauma Injury, Infection and Critical Care (2007) pp. 94-103.
Sondeen, J. et al, 'Comparison of 10 Different Hemostatic Dressings in an Aortic Injury' Journal of Trauma, Injury, Infection and Critical Care (2003) pp. 280-285.

*Primary Examiner* — Ernst Arnold
(74) *Attorney, Agent, or Firm* — David R. Crichton

(57) ABSTRACT

The present invention is directed to a reinforced absorbable hemostat comprising at least one hemostatic agent in a single layer of nonwoven synthetic fabric having a mixture of compressed fiber staples of a polyglycolide/polylactide copolymer and a polydioxanone.

12 Claims, No Drawings

REINFORCED ABSORBABLE SYNTHETIC MATRIX FOR HEMOSTATIC APPLICATIONS

This application is a division of copending U.S. patent application Ser. No. 12/781,103, which was filed on May 17, 2010. The complete disclosures of the aforementioned related U.S. patent applications are hereby incorporated herein by reference.

FIELD OF THE INVENTION

The present invention relates to a bioabsorbable hemostat device that is useful as a construct for use in medical devices.

BACKGROUND OF THE INVENTION

The control of bleeding is essential in surgical procedures to improve the outcomes and to shorten the duration of the surgery in the operating room. Several hemostatic materials including oxidized cellulosic based material has been used as a dressing in a variety of surgical procedures, including neurosurgery, abdominal surgery, cardiovascular surgery, thoracic surgery, head and neck surgery, pelvic surgery and skin and subcutaneous tissue procedure.

It is generally accepted to use multilayered fabrics in connection with medical procedures. For example, multilayered fabrics are used as all purpose pads, wound dressings, surgical meshes, including hernia repair meshes, adhesion prevention meshes and tissue reinforcement meshes, defect closure devices, and hemostats.

U.S. Pat. No. 5,593,441 to Lichtenstein et al describes a composite prosthesis preferably having a sheet of polypropylene mesh that allows tissue in-growth, such as Marlex® mesh. This reference discloses that other surgical materials that are suitable for tissue reinforcement and defect closure may be utilized, including absorbable meshes such as polyglactin 910 (Vicryl®) mesh. The composite prosthesis of Lichtenstein et al also has an adhesion barrier, preferably a sheet of silicone elastomer. This reference generally suggests that that an oxidized regenerated cellulose such as Interceed® (TC7) absorbable adhesion barrier (commercially available from Ethicon, Inc., in Somerville, N.J.) may be used as the adhesion barrier to produce a composite prosthesis having short term effectiveness.

U.S. Pat. No. 5,686,090 to Schilder et al describes the use of a fleece in combination with a nonabsorbable or absorbable film to prevent mis-growths to adjacent tissue and to reduce adhesions. Schilder et al generally discloses that polypropylene, polyester, polyglactin, polydioxanone or poliglecaprone 25 may be used as the fleece material or the film material. Published U.S. Patent Application 2006/00084930, to Dhanaraj et al, describes a reinforced absorbable multilayered fabric that can be used in medical devices specifically for tissue engineering applications. The matrix comprises first preparing a repair site for implantation, and then disposing the reinforced absorbable multilayered fabric at site. The first absorbable nonwoven fabric comprises fibers comprising aliphatic polyester polymers, copolymers or blends thereof; while the second absorbable woven or knitted fabric comprises oxidized regenerated cellulose fibers. Although the cells are seeded onto the 9010 PLGA component of the matrix before it migrates through the nonwoven matrix and comes in contact with the ORC component. The ORC component typically breaks down in about two weeks and the degradation components create an acidic environment that may not be conducive to cell proliferation or viability. The present invention addresses that by having a totally absorbable synthetic matrix that does not create such environment that is not conducive for cell viability U.S. Pat. No. 4,626,253 to Broadnax et al, describes a device that relates to a surgical hemostat (SURGICEL) for control of bleeding, and more particularly, to a knitted fabric of oxidized cellulose having superior handling and hemostatic properties. U.S. Pat. No. 7,666,803 to Shetty et al. describes the method of making or reinforced absorbable multilayered fabric that can be used as a hemostat. The matrix comprises first preparing a repair site for implantation, and then disposing the reinforced absorbable multilayered fabric at site. The first absorbable nonwoven fabric comprises fibers comprising aliphatic polyester polymers, copolymers or blends thereof; while the second absorbable woven or knitted fabric comprises oxidized regenerated cellulose fibers. The method also describes the appropriate densities and thickness that can be used to make the matrix in that particular invention. However in certain applications where both the hemostasis function and an increased mechanical property is required over a longer period of time, the matrix mentioned will not satisfy both the requirements primarily due to its weaker mechanical properties.

Published U.S. patent application 2008/0033333 to MacPhee et al describes the use of DEXON (polyglycolic acid woven matrix) as a backing material for fibrinogen and thrombin, U.S. Pat. No. 6,762,336 describes the use of glycolic acid or lactic acid based polymers or copolymers (VICRYL) as one layer to support the sandwich layers of fibrinogen and thrombin. Similarly, fibrin sealant pads that were described as developed by the American Red Cross are described in various articles, such, the The Potential Utility of Fibrin Sealant Dressing in Repairing of Vascular Injury in Swine, Bijan Kheirabadi et al., Journal of Trauma Injury, Infection and Critical Care, January 2007, pp. 94-103 and Comparison of 10 Different Hemostatic Dressings in an Aortic Injury, Jill Sondeen et al., Journal of Trauma, Injury, Infection and Critical Care, February 2003, pp. 280-285.

SUMMARY OF THE INVENTION

The present invention is directed to a reinforced absorbable hemostat comprising a single layer of nonwoven synthetic fabric. The absorbable nonwoven fabric is comprised of fibers comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, epsilon-caprolactone, p-dioxanone (1,4-dioxan-2-one), and trimethylene carbonate (1,3-dioxan-2-one). In one embodiment, the non-woven synthetic fabric consists essentially of a blend of a polyglycolide/polylactide copolymer and polydioxanone. The present invention is further directed to a hemostatic fabric comprising at least one hemostatic agent in a non-woven layer of a first absorbable fabric that comprises polyglycolide/polylactide copolymer and a second absorbable fabric that comprises polydioxanone, wherein both fabrics are in staple form.

The first absorbable fabric can consist essentially of a copolymer of glycolide/lactide at a 90/10 mol/mol composition. The first absorbable fabric can be in the form of a staple having a length from about 0.75 to 2.5 inches. The second absorbable fabric can be in the form of a staple having a length from 0.75 to 2.5 inches. One or both of these staples can be crimped, chemically or mechanically. The weight ratio of the first fabric staples to the second fabric staples can be about 70:30. The mixture of staple materials can be compacted to a thickness of about 1.5 mm and a density of about 100 mg/cc.

In one embodiment, the hemostatic device is substantially free of any oxidized polysaccharide material. In one embodiment, the hemostatic agent comprises thrombin. In another embodiment, the hemostatic agent on the hemostatic device comprises thrombin and fibrinogen.

The present invention is also directed to a method for using the hemostatic fabric described above as a medical device. The medical device described above preferably provides hemostasis when applied to a tissue or wound requiring hemostasis. More particularly, the device can control and abate mild to moderate bleeding within an effective time period of from about 1 to about 10 minutes.

The present invention is also directed to a method for manufacturing a hemostatic fabric described above comprising the steps of suspending the thrombin and fibrinogen In a perfluorinated hydrocarbon to form a suspension and applying the suspension to the absorbable nonwoven fabric. The thrombin activity on the hemostatic fabric can range from about 20 to 500 IU/cm2, and the fibrinogen on the dressing can range from about 2 to 15 mg/cm2. The method can further include the step of sterilizing the hemostatic fabric, such as by radiation.

DETAILED DESCRIPTION OF THE INVENTION

The reinforced absorbable fabric is a non-woven material that comprises at least two synthetic polymer fibers and one or more hemostatic agents. The fabric preferably does not include material amounts of cellulosic or oxidized polysaccharides as a separate layer or combined as part of the nonwoven layer. Examples of cellulosic or oxidized, polysaccharides that have previously been used in hemostatic devices include oxidized cellulose and the neutralized derivatives thereof. For example, the cellulose may be carboxylic-oxidized or aldehyde-oxidized cellulose. Regenerated cellulose and a detailed description of how to make oxidized regenerated cellulose is set forth in U.S. Pat. No. 3,364,200, U.S. Pat. No. 5,180,398, and U.S. Pat. No. 4,626,253, the contents each of which is hereby incorporated by reference as if set forth in its entirety. While such cellulosic derived materials have been shown to enhance hemostasis, the present invention enjoys certain advantages, particularly when used in combination with particulate-form or lyophilized hemostatic agents, such as thrombin and fibrinogen.

The first absorbable nonwoven fabric is comprised of fibers comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, epsilon-caprolactone, p-dioxanone (1,4-dioxan-2-one), and trimethylene carbonate (1,3-dioxan-2-one). In one embodiment, the first polymeric fiber material consists essentially of a blend of copolymer of glycolide and lactide, such as a copolymer poly(glycolide-co-lactide) (PGLA, 90/10 mol/mol) and polydioxanone (PDO). The two materials are processed into a single layer of nonwoven fiber material and are preferably combined at a weight ratio of about 80:20 to about 60:40, more preferably about 70:30 of PGLA and PDO. The PLGA to PDO weight ratio in the nonwoven blend can be from 10:90 to 90:10, most preferably in the range of 70:30.

In one embodiment, poly (glycolide-co-lactide) (PGLA, 90/10 mol/mol) is melt-spun into a polymeric fiber. A multi-filament yarn of PGLA is consolidated, crimped and cut into staple having a length of 0.1 to 3.0 inches, preferably between 0.75 to 2.5 inches. PDO is melt-spun into polymeric fiber. A multi-filament yarn of PDO is consolidated, crimped and cut into staple having a length of 0.1 to 3.0 inches, preferably between 0.75 to 2.5 inches. The mixture of these staple materials consisting essentially of PGLA/PDO with a weight ratio of 70/30 was carded to create a nonwoven batt and then compacted to a thickness of about 0.25 to 2.5 mm, preferably 1.25 to 1.75 mm and a density of 50 to 200 mg/cc, preferably 75 to 125 mg/cc.

One method of making the fabric described herein is by the following process. Absorbable polymer fibers, having a size of denier per fiber of about 1 to 4, can be consolidated to about 80 to 120 denier multifilament yarn and then to about 800 to 1200 denier yarn, thermally crimped and then cut to staple having a length between about 0.75 and 2.5 inch. The staple can be fed into a multi-roller dry lay carding machine one or more times and carded into a uniform nonwoven batt, while humidity is controlled between, about 20-60% at a room temperature of 15 to 24° C. For example, the uniform nonwoven batt can be made using a single cylinder roller-top card, having a main cylinder covered by alternate rollers and stripper rolls, where the batt is doffed from the surface of the cylinder by a doffer roller and deposited on a collector roll. The reinforced absorbable fabric can then be scoured by washing in an appropriate solvent and dried under mild conditions for 10-30 minutes.

The fabric is scoured using solvents suitable to dissolve any spin finish. Solvents include, but are not limited to, isopropyl alcohol, hexane, ethyl acetate, and methylene chloride. The fabric is then dried under conditions to provide sufficient drying while minimizing shrinkage.

The hemostat described herein provides and maintains effective hemostasis when applied to a wound requiring hemostasis. Effective hemostasis, as used herein, is the ability to control and/or abate mild to moderate bleeding within an effective time, as recognized by those skilled in the art of hemostasis. Further indications of effective hemostasis may be provided by governmental regulatory standards and the like. Examples of mild to moderate bleeding include, without limitation, bleeding due to spleen resection, liver resection, blunt liver trauma, and blunt spleen trauma.

The non-woven substrate described above cast include one or more hemostatic agents. Hemostatic agents, for purposes of this application, am agents that have a hemostatic effect, more preferably, slow, impede and eventually stop bleeding at the site of the injury. One method for producing a hemostatic effect at the site of an injury is to introduce one or more agents found in the blood clotting cascade process that may react with one another or other agents naturally present in the body. Thrombin has been used for producing a hemostatic effect, while in another embodiment, thrombin and fibrinogen are used together to produce the desired hemostatic effect. Additional components, such as calcium, can also be provided to further enhance the hemostatic effect.

In one embodiment, the bioabsorbable nonwoven fabric retains solid thrombin and/or solid fibrinogen in powdery, particulate form without separation and with minimal loss of the powder from its surface due in part to the means for the addition of the hemostatic agent(s) and the non-woven nature of the substrate. In a preferred method for applying thrombin and/or fibrinogen to the matrix, one or more biologics containing solutions are separately lyophilized. The lyophilized materials are then ground into powders using a superfine mill, ball mill or a cooled blade mill. The powders am weighed and suspended together in a carrier fluid in which the proteins are not soluble. A preferred carrier fluid is a perfluorinated hydrocarbon, including but not limited to HFE-7000, HFE-7100, HFE-7300 and PF-5060 (commercially available from 3M of Minnesota). Any other carrier fluid in which the proteins do not dissolve may be used, such as alcohols, ethers or other organic fluids. The suspension is thoroughly mixed and applied to the absorbable nonwoven fabric via conventional means such as wet, dry or electrostatic spraying, dip coating, painting, or sprinkling, while maintaining a room temperature of about 15 to 24° C. and relative humidity of about 10 to 60%, preferably no more than 30%. The single layer dressing is then dried at ambient room temperature and packaged in a suitable moisture barrier container. The dressing having the thrombin and/or fibrinogen contains no more than 25% moisture, preferably no more than 15% moisture, and most preferably no more than 5% moisture.

The thrombin and/or fibrinogen may be animal derived, human, or may be recombinant. The thrombin activity on the dressing may be in the range of about 20 to 500 $IU/cm^2$, preferably about 20 to 200 $IU/cm^2$, and most preferably about 50 to 200 $IU/cm^2$. The fibrinogen activity on the dressing may be in the range of about 2 to 15 $mg/cm^2$, preferably about 3 to 12 $mg/cm^2$, and most preferably about 5 to 10 $mg/cm^2$. The amount of thrombin and/or fibrinogen powder is preferably applied to the nonwoven fabric in a sufficient amount to cover its surface such that no area is visibly devoid of coverage. The powder may sit mostly on top of the nonwoven fabric or, more preferably penetrates into the nonwoven fabric.

As a surgical dressing, the dressing described herein may be used as an adjunct to primary wound closure devices, such as arterial closure devices, staples, and sutures, to seal potential leaks of gasses, liquids, or solids as well as to provide hemostasis. For example, the dressing may be utilized to seal air from tissue or fluids from organs and tissues, including but not limited to, bile, lymph, cerebrospinal fluids, gastrointestinal fluids, interstitial fluids and urine.

The hemostat described herein has additional medical applications and can be used for a variety of clinical functions, including but not limited to matrix/substrate, i.e., fibrinogen/thrombin coating, tissue reinforcement, and buttressing, i.e., for gastrointestinal or vascular anastomoses, approximation, i.e., to connect anastomoses that are difficult to perform (i.e. under tension), and tension releasing. The hemostat matrix can additionally promote and possibly enhance the natural tissue healing process in all the above events. This dressing can be used internally in many types of surgery, including, but not limited to, cardiovascular, peripheral-vascular, cardio-thoracic, gynecological, neuro- and general surgery. The hemostat can also be used to attach medical devices (e.g. meshes, clips and films) to tissues, tissue to tissue, or medical device to medical device.

Example 1

A Single Layer Matrix of PGLA/PDO

Poly (glycolide-co-lactide) (PGLA, 90/10 mol/mol) is melt-spun into polymeric fiber. A mufti-filament yarn is consolidated, crimped and cut into PGLA staple material having a length of 2.0 inches. Polydioxanone (PDO) is melt-spun into polymeric fiber. A mono-filament yarn is consolidated, crimped and cut into PDO staple material having a length of 2.0 inches. The mixture of staple materials of PGLA/PDO are combined at a weight ratio of 70/30 and are carded to create a nonwoven batt and then compacted to a thickness of about 1.5 mm and a density of about 100 mg/cc.

Example 2

A mild to moderate bleeding model was created by making an incision of 15 mm long and 3 mm deep on a swine spleen. One PGLA/PDO matrix as described in Example 1 is applied to the surgical site and tamponade is applied for two minutes. Hemostasis is checked for 30 seconds after the two-minute tamponade. If free flow bleeding is not observed within 30 seconds, the time to hemostasis was noted. If free flow bleeding is observed, a 30-second tamponade is reapplied until hemostasis is achieved or until the testing period reaches ten minutes, which is defined as a failure in hemostasis. All three test samples achieved hemostasis at 3.14±1.26 minutes (Table 1).

TABLE 1

Hemostasis of PGLA/PDO matrix in spleen model

| Sample # | 1 | 2 | 3 | Mean | SD |
|---|---|---|---|---|---|
| Hemostasis (min) | 2.00 | 2.92 | 4.50 | 3.14 | 1.26 |

Example 3

The mechanical property of the reinforced fabric is characterized in an in vitro test. The PGLA/PDO matrix material described in Example 1 is cut into strips (approximately ⅜ inch wide by 2 inches long). The tensile strength of the fabric is then evaluated at dry and wet conditions using an Instron Tensile Analyzer. Under wet conditions, strips are placed in a conical tube containing PBS buffer pH 7.4 at 37° C. The tensile strength of the strips is then measured at 120 minutes, 4 days, 7 days, 11 days, and 14 days. The tensile strength values of the PGLA/PDO materials, as described in Example 1, are shown in Table 2.

TABLE 2

Tensile strength of PGLA/PDO in dry and wet conditions

| | Dry | 120 min | 4 days | 7 days | 11 days | 14 days |
|---|---|---|---|---|---|---|
| Tensile Strength (Newton/cm) | 63.2 ± 10.7 | 58.6 ± 4.8 | 50.3 ± 3.7 | 35.3 ± 6.7 | 17.5 ± 4.9 | 11.0 ± 2.0 |

Example 4

A hemostatic device that combines the PGLA/PDO matrix material and one or more hemostatic agents can be prepared by coating fibrinogen and thrombin onto the PGLA/PDO matrix material of Example 1 for tire management of severe bleeding. Such a "Combination Product" is constructed by coating porcine fibrinogen and thrombin onto the PGLA/PDO matrix as described in Example 1. The PGLA/PDO matrix is cut into the size of 5×10 cm and sterilized by gamma-irradiation (25 to 35 kGy). Varying amount of porcine fibrinogen and thrombin (see table 3) are mixed thoroughly with about 6.5 ml of HFE-7000. The slurry is poured into a 5.5×10.5 cm tray and the PGLA/PDO matrix is immersed in the tray. The coated hemostatic devices are air dried for about 30 minutes. The environmental conditions are maintained at 24 C and 45% RH throughout the process. The dressing is vacuum-dried and packed in plastic bag with nitrogen gas. The packed dressing is sterilized again by electronic beam (8 to 12.5 kGy). The efficacy of the dressing is tested in severe bleeding model (swine partial nephrectomy model). The results are presented in Table 3.

TABLE 3

Hemostasis of PGLA/PDO with different levels of fibrinogen and thrombin

| Sample ID | Matrix | Fibrinogen (mg/cm$^2$) | Thrombin (IU/cm$^2$) | Hemostasis (min) |
|---|---|---|---|---|
| A | PGLA/PDO | 0 | 0 | 9.5 ± 4.0 |
| B | PGLA/PDO | 0 | 100 | 6.5 ± 5.2 |
| C | PGLA/PDO | 9 | 0 | 6.1 ± 2.2 |
| D | PGLA/PDO | 5 | 20 | 3.8 ± 1.6 |
| E | PGLA/PDO | 5 | 50 | ≦3.0 |
| F | PGLA/PDO | 5 | 100 | 3.8 ± 1.5 |
| G | PGLA/PDO | 9 | 20 | 6.1 ± 0.1 |
| H | PGLA/PDO | 9 | 50 | 6.2 ± 0.1 |
| I | PGLA/PDO | 9 | 100 | 6.2 ± 2.6 |

Example 5

Poly (glycolide-co-lactide) (PGLA, 90/10 mol/mol) is melt-spun into polymeric fiber. A multi-filament yarn is consolidated, crimped and cut into PGLA staple material having a length of 2.0 inches. The staple materials of PGLA are carded to create a nonwoven batt and compacted to a thickness of about 2.3 mm and a density of about 59 mg/cc. A mild to moderate bleeding model was created by making an incision of 15 mm long and 3 mm deep on a swine spleen. The PGLA matrix is applied to the surgical site and tamponade is applied for two minutes. Hemostasis is checked for 30 seconds after the two-minute tamponade. If free flow bleeding is not observed within 30 seconds, the time to hemostasis was noted. If free flow bleeding is observed, a 30-second tamponade is reapplied until hemostasis is achieved or until the testing period reaches ten minutes, which is defined as a failure in hemostasis. Two samples were tested and both achieved hemostasis (5.5 and 4.75 minutes).

We claim:

1. A method for treating a wound or tissue comprising applying a synthetic hemostatic fabric comprising at least one hemostatic agent in a non-woven layer of a first absorbable fabric that comprises polyglycolide/polylactide copolymer and a second absorbable fabric that comprises polydioxanone, wherein both fabrics are in staple form.

2. The method of claim 1, where the first absorbable fabric consists essentially of a copolymer of glycolide/lactide at a 90/10 mol/mol composition.

3. The method of claim 2, where the first absorbable fabric comprises of staple having a length from about 0.75 to 2.5 inches.

4. The method of claim 1 that is substantially free of any oxidized polysaccharide material and the hemostatic agent comprises thrombin.

5. The method of claim 1, where the staple is crimped.

6. The method of claim 4, where the second absorbable fabric comprises of staple having a length from 0.75 to 2.5 inches.

7. The method of claim 6, where the staple is crimped.

8. The method of claim 4, where the hemostatic agent further comprises fibrinogen.

9. The method of claim 1, where the weight ratio of the first fabric staples to the second fabric staples is 70:30.

10. The method of claim 9, where the mixture of the staples is compacted to a thickness of about 1.5 mm.

11. The method of claim 10, where the mixture of the staples is compacted to a density of about 100 mg/cc.

12. A method according to claim 1 wherein the medical device provides hemostasis when applied to a tissue or wound requiring hemostasis.

* * * * *